United States Patent [19]

Reinert

[11] Patent Number: 5,044,359

[45] Date of Patent: Sep. 3, 1991

[54] PASSIVE SPINAL EXTENSION DEVICE

[76] Inventor: Otto C. Reinert, 2024 Long Gate Ct., Chesterfield, Mo. 63017

[21] Appl. No.: 536,724

[22] Filed: Jun. 12, 1990

[51] Int. Cl.[5] .................................................. A61F 5/00

[52] U.S. Cl. .................................... 128/74; 128/25 R; 128/71

[58] Field of Search .................... 128/25 R, 70, 71, 74, 128/73, 75; 272/123, 134, 144; 269/323, 324, 325

[56] References Cited

U.S. PATENT DOCUMENTS

| | | | |
|---|---|---|---|
| 2,091,014 | 8/1937 | Saak | 269/325 X |
| 2,358,254 | 9/1944 | Sanders | 128/25 R |
| 2,494,746 | 1/1950 | Colston | 128/25 R |
| 2,553,969 | 5/1951 | Hien et al. | 128/75 |
| 3,771,518 | 11/1973 | Greissing | 128/71 |
| 3,821,953 | 6/1974 | Mikan | 128/71 |
| 4,097,037 | 6/1978 | Tardiff | 269/323 |
| 4,587,961 | 5/1986 | Ventura et al. | 128/25 R |
| 4,649,905 | 3/1987 | Barnes | 128/74 |
| 4,750,741 | 6/1988 | Smolanovich | 272/144 |
| 4,850,343 | 7/1989 | Scott | 128/70 X |

FOREIGN PATENT DOCUMENTS

| | | | |
|---|---|---|---|
| 0316209 | 5/1989 | European Pat. Off. | 272/144 |
| 1226506 | 2/1960 | France | 272/144 |

OTHER PUBLICATIONS

Campbell, "Clinix X-Ray Plant", Cat. No. 2087, 9/28/1921.

*Primary Examiner*—Richard J. Apley
*Assistant Examiner*—Jennifer L. Doyle
*Attorney, Agent, or Firm*—Senniger, Powers, Leavitt & Roedel

[57] ABSTRACT

A device for passive extension of the spine including first and second support panels abutting in end to end alignment for supporting a person's body in a prone position. The upper portion of the person's body is supported on the first panel and the lower portion of the person's body supported on the second panel. The first panel is pivotable with respect to the second panel about a transverse axis. A selected area in the lumbar or sacrum region of the spine is positioned over the transverse axis. The first panel supports the head of the person lying face down on the panel while providing clearance for the nose and mouth. The first panel and the portion of the person's body supported on it may be held at a selected angular position with respect to the second panel thereby holding the person's spine in a selected angle of extension. The angle between the first and second panels, and thus the approximate angle of extension of the spine, may be read directly from the device.

14 Claims, 4 Drawing Sheets

PASSIVE SPINAL EXTENSION DEVICE

BACKGROUND OF THE INVENTION

This invention relates generally to apparatus for the treatment of the back and more particularly to a device for treatment of the back through passive spinal extension.

Persons suffering from low back pain frequently lose flexibility in the lower back in the direction of spinal extension. It has been found that flexibility may be increased through passive bending of the lower back in extension. In passive bending, the person does not use any of his own muscles to produce the bending, but rather remains relaxed while his body is acted upon externally.

This treatment may be particularly effective when the cause of the low back pain is damage to the circumferential fibers which retain a central mass of gel ("nuclear mass") in the disc between adjacent vertebrae. Such damage may result in a shifting of the mass of gel toward the posterior and posterior-lateral and a tilting of the upper vertebrae toward the anterior and anterior-lateral. A victim of this type of injury cannot stand fully erect and may be unable to lie down because of the dislocation of the nuclear mass. Correction and subsequent control of the disorder may require manipulation of the spine to restore the nuclear mass toward its normal central location, or surgery to remove the displaced mass. Passive spinal extension enhances corrective processes by compressing the disc at the posterior, squeezing against the nuclear mass and encouraging its movement toward its normal position near the center between adjacent vertebrae. Passive spinal extension both facilitates restoration of the nuclear mass position and measures the success of other corrective steps through observation of increases in the patient's flexibility in the direction of spinal extension.

Thus there is presently a need for a device to treat the lower back through passive spinal extension.

SUMMARY OF THE INVENTION

Among the several objects of the present invention may be noted the provision of a passive spinal extension device which holds the spine at the selected angle of extension; the provision of such a device which indicates the capacity of the patient to comfortably extend the lumbar spine; the provision of such a device which is adjustable to accommodate persons of different heights and to accommodate different treatment positions; and the provision of such a device which comfortably supports a person lying prone thereon.

Generally a passive spinal extension device of the present invention comprises a base and first and second support panels on the base abutting in end to end alignment for supporting a person's body in a prone position. The first panel is adapted-to pivot about a transverse axis with respect to the second panel. The upper portion of the person's body is supported on one of the panels, and the lower-portion of the person's body is supported on the other of the panels with a selected point in the lumbar or sacrum region of the spine generally located over the transverse axis. The first panel is adapted to support the head of the person lying face down thereon while providing clearance for the nose and mouth. Means is provided for holding the first panel and the portion of the person's body supported thereon at a selected angular position with respect to the second panel thereby holding the person's spine at a selected angle of extension. The device has means for indicating the approximate degree of extension of the spine.

Other objects and features will be in part apparent and in part pointed out hereinafter.

BRIEF DESCRIPTION OF THE DRAWINGS

Corresponding reference characters indicate corresponding parts throughout the several views of the drawings.

BRIEF DESCRIPTION OF A PREFERRED EMBODIMENTS

Figures 1, 5:
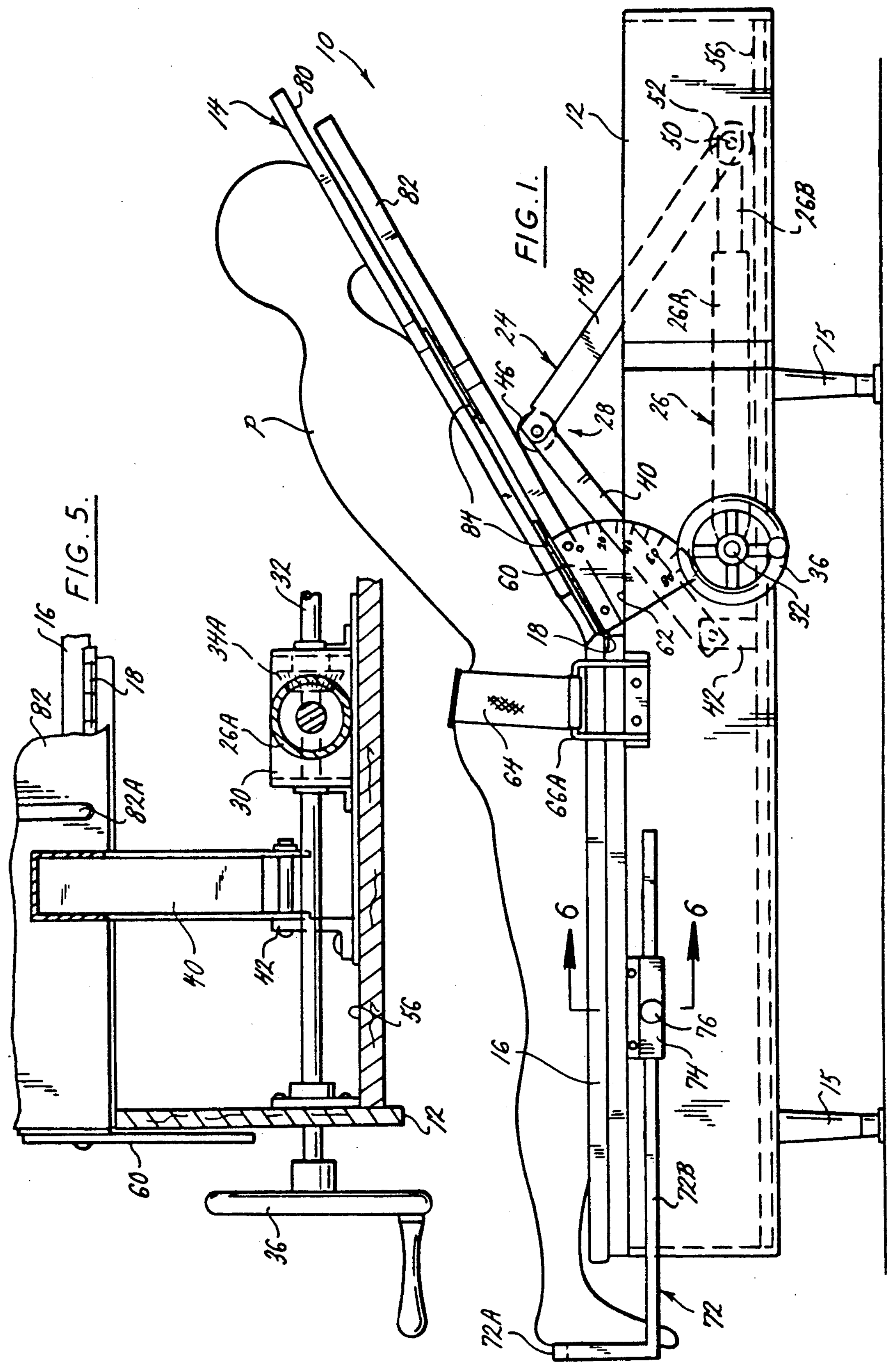
FIG. 1 is an elevation of the device of the present invention showing a person lying in a prone position thereon.
FIG. 5 is a fragmentary section taken in the plane including line 5—5 of FIG. 3.

Referring now to the drawings, a device of a first embodiment, indicated generally at 10, for passive extension of a person's spine is shown to comprise a base 12, a first support panel 14 and a second support panel 16. The panels 14, 16 lie on the base 12 in end to end alignment. The base 12 includes legs 15 which space the remainder of the base from the floor. The first panel 14 is connected to the base 12 and the second panel 16 by a hinge 18 which allows the first panel to pivot about a transverse axis A with respect to the second panel. The panels 14, 16 support the body of a person P lying in a prone position on the device 10. As shown in FIG. 1, the upper portion of the person's body is supported on the first panel 14 and the lower portion of the person's body is supported on the second panel 16. Means, indicated generally at 24, holds the first panel 14 and the portion of the person's body supported on the first panel at a selected angular position with respect to the second panel 16. The device 10 supports the person in a position, as may seen in FIG. 1, which places the person's spine in extension.

Figures 3, 4:
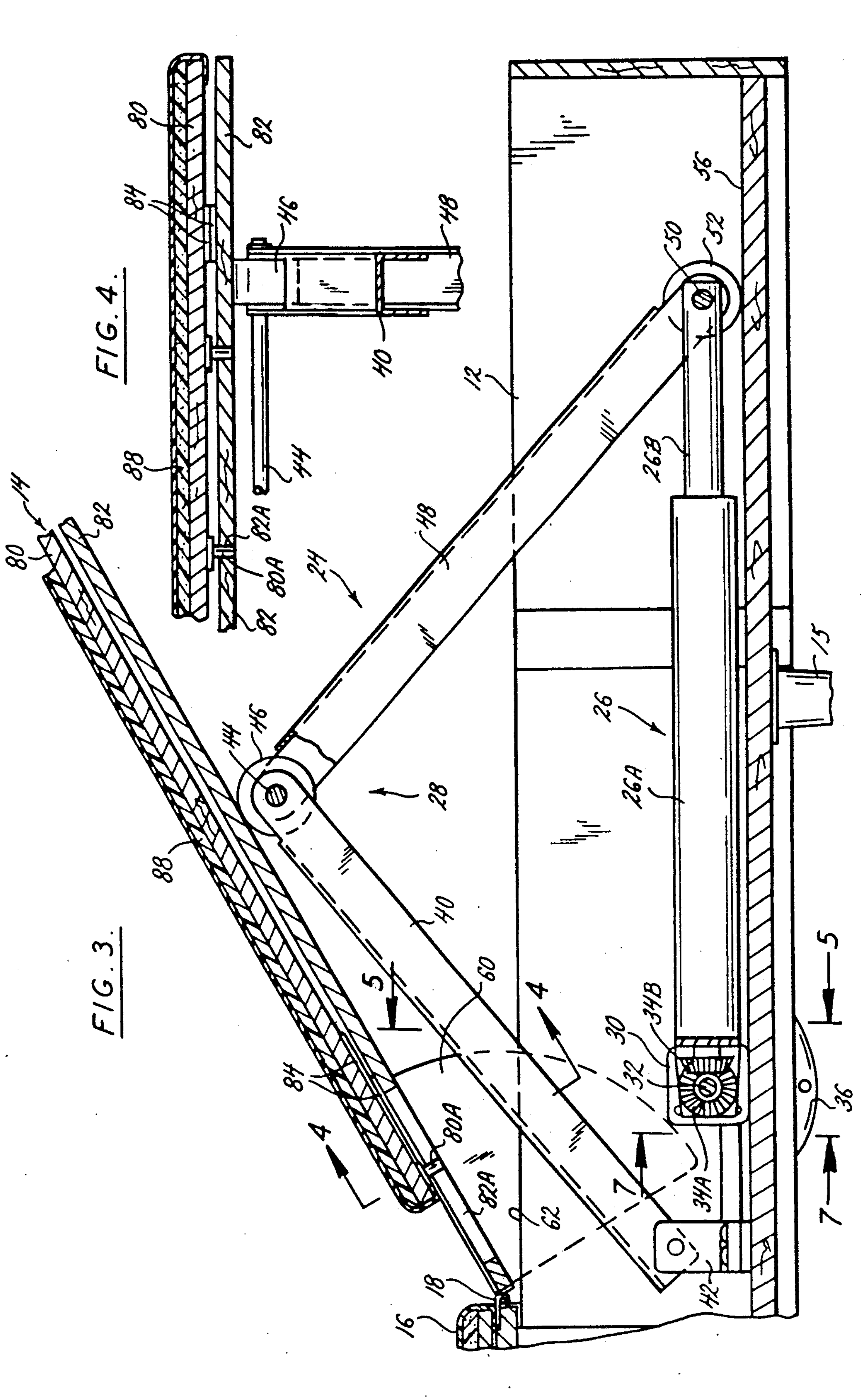
FIG. 3 is a fragmentary section taken in the plane including line 3—3 of FIG. 2.
FIG. 4 is a fragmentary section taken in the plane including line 4—4 of FIG. 3.

The holding means 24 of the first embodiment also constitutes pivoting means adapted to pivot the first panel 14 about the transverse axis A. As best seen in FIG. 3, the holding means 24 includes a jack 26 lying horizontally in the base 12 under the first panel 14, and a linkage 28 adapted to engage the underside of the first panel. The jack 26 in the device illustrated in the drawings is a trailer jack, including a cylinder 26A, which is fixed to the base 12 at one end by a bracket 30, and an arm 26B telescopically received in the cylinder. A shaft 32 extends transversely through the base 12 and through the bracket 30. At the bracket 30, the shaft has a bevel gear 34A mounted on it which is enmeshed with a bevel gear 34B connected to the jack 26. Cranks 36 are mounted on the ends of the shaft 32 on opposite sides of the base 12 for turning the shaft. Rotation of the shaft 32 and hence of the bevel gears 34A, 34B in a first direction extends the arm 26B from the cylinder 26A, and rotation of the shaft and bevel gears in a second, opposite direction retracts the arm into the cylinder.

Figure 2:
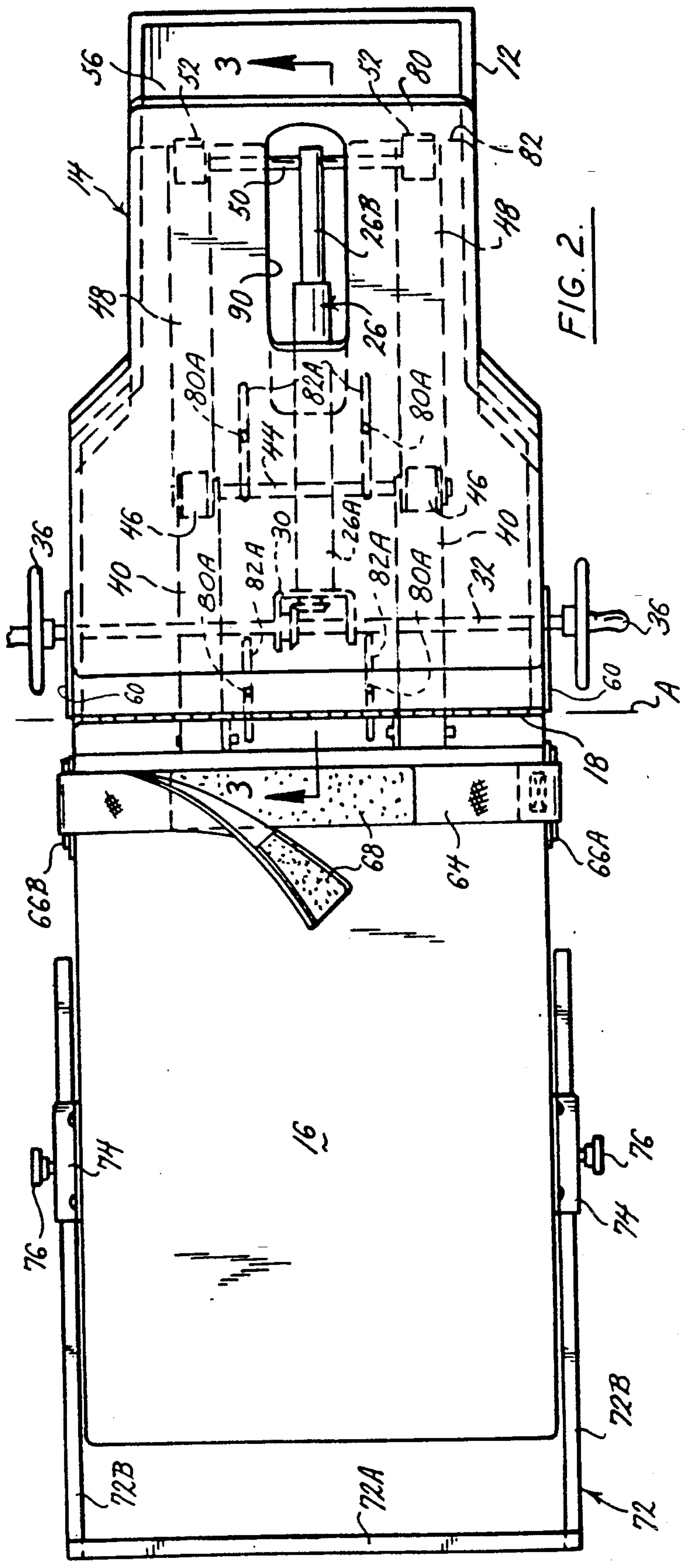
FIG. 2 is a top plan view of the device with the upper section of the first panel removed.
Figure 7:
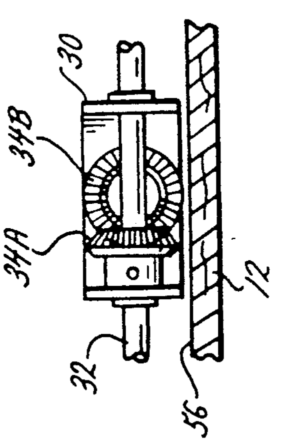
FIG. 7 is a fragmentary section taken in the plane including line 7—7 of FIG. 1.

The linkage 28 includes a first pair of links 40 pivotally connected at one end to lugs 42 mounted on the base 12. As shown in FIG. 2, the other ends of the first links 40 are connected to a first axle 44 rotatably supporting a first pair of laterally spaced apart rollers 46. One end of each of a second pair of links 48 is also pivotally connected to the first axle 44, with the opposite end being pivotally connected to a second axle 50 rotatably mounting a second pair of rollers 52. As best seen in FIG. 3, the second pair of rollers 52 support the free end of the arm 26B and allow it to move easily across a surface 56 in the base 12 . Referring now again to FIG. 3, it may be seen that upon retraction of the arm 26B into the cylinder 26A, the links 40, 48 fold together about an axis corresponding to the first axle 44. The first pair of rollers 46 move upwardly engaging the underside of the first panel 14 causing it to pivot upwardly on the hinge 18 about the transverse axis A. Extension of the arm 26B from the cylinder 26A unfolds the links 40, 48, moving the first pair of rollers 46 down into the base 12 and bringing the first panel 14 to a generally horizontal position.

The jack 26 and linkage 28 are configured for pivoting the first panel 14 with respect to the second panel 16 in a range from 0° to not substantially greater than 60° with respect to the second panel 16. The first panel 14 and the weight of the upper portion of the person's body supported thereon will be held in any selected angular position in this range by the jack 26. The angle the first panel 14 makes with the base 12, and thus with the second panel 16, is measured by a transparent, pie-shaped members 60 (FIG. 1). The transparent members 60, which constitute indicating means in this embodiment, are attached to opposite sides of the first panel 14 for motion with the first panel relative to the base 12. The transparent members 60 are each ruled in degrees along its arcuate edge, and the angle of the first panel 14 is read through the transparent member to the top edge 62 of a side wall of the base 12 (FIG. 1). It is to be understood that the angle may be measured in other ways and still fall within the scope of the present invention.

Restraining means, constituting in the preferred embodiment a strap 64, restrains a portion of the person's body generally adjacent the line of abutment between the panels 14, 16 against the second panel 16. The strap 64, which is secured to a metal ring 66A affixed to the base 12 on one side, passes over the buttocks (or lower back) and through a metal ring 66B on the opposite side of the base. By pulling the free end of the strap 64 through the ring 66B, the strap is tightened down against the buttocks to restrain the pelvic region of the body against the second panel 16. The strap 64 is suitably secured to maintain a restraining force against the buttocks. In the preferred embodiment, a hook and loop type fastener 68, commonly referred to by the trademark VELCRO, is employed to secure the free end of the strap 64 to a middle portion of the strap (FIG. 2). Thus, pivoting the first panel 14 results in bending the back in extension rather than bending in combination with lifting the lower portion of the person's body off the second panel 16. Therefore, the angle the first panel 14 makes with the base 12, as indicated by the transparent member 60, corresponds to the angle of extension of the spine.

Figure 6:
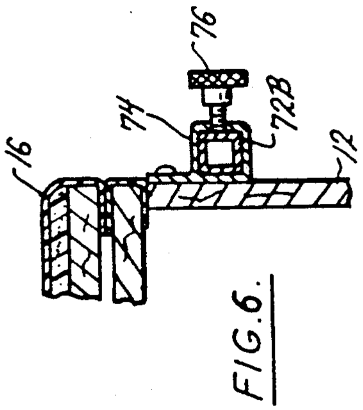
FIG. 6 is a fragmentary section taken in the plane including line 6—6 of FIG. 1 showing an adjustment sleeve for the foot stop of the present invention.

Although the strap 64 prevents the pelvic region from being lifted off the second panel 16 as the first panel 14 is pivoted upwardly, the body also tends to move longitudinally toward the foot of the base 12. This motion displaces the area of the back to be treated, which is initially positioned over the transverse axis A. To prevent this motion, a stop 72 is provided at the foot of the base 12 which is engageable with a portion of the body (e.g., the feet) to hold the body from sliding toward the foot of the base 12. The stop 72 includes a cross bar 72A located to the left (as seen in FIG. 1) of the foot of the base 12 for engaging the person's feet, and a pair of arms 72B extending inwardly on each side of the base 12 and received through sleeves 74 mounted on the base. Referring now to FIG. 6, a set screw 76 in the side of the sleeve 74 is screwed down against the arm 72B to hold it in a fixed position. To adjust the position of the stop 72, the screw 76 is loosened, and the arms 72B slid through the sleeve 74 until the cross bar 72A is appropriately positioned.

The upper portion of the person's body also tends to move toward the end of the first panel 14 opposite the second panel 16 as the first panel is pivoted upwardly. As shown in FIG. 3, the first panel 14 includes an upper section 80 and a lower section 82. The upper section 80 is adapted for movement with respect to the lower section 82 in the plane of the first panel 14 to accommodate movement of the upper portion of the person's body. The lower section 82 is attached by the hinge 18 to the second panel 16 and to the base 12. The pivot axis of the hinge 18 coincides with the transverse axis A and is closely adjacent the line of abutment between the first panel 14 and the second panel 16. As shown in FIGS. 3 and 4, the upper section 80 has a pair of laterally spaced pins 80A depending from it which are received in corresponding elongate slots 82A in the lower section 82. These slots 82A serve as tracks which constrain the motion of the upper section 80 to generally longitudinally of the lower section 82. The slots 82A also limit the maximum relative longitudinal motion of the upper and lower sections 80, 82. The bearing surfaces of the upper and lower sections are strips 84 of low friction material attached to the upper and lower sections 80, 82, respectively, and overlying one another (FIG. 4). These strips 84 allow the upper section 80 to glide easily over the lower section 82 as the upper portion of the body moves toward the upper end of the first panel 14.

The panels 14, 16 include a layer of padding material 88 on their upper surfaces for the comfort of the person being treated, who may have to lie in a prone position on the device 10 for several minutes. For additional comfort of the person, the first panel 14 is adapted to support his head while providing clearance for the nose and mouth. An elongate opening 90 through the upper and lower sections 80, 82 of the first panel 14 receives a portion of the person's face including specifically the nose and mouth. Therefore, the person may remain in a face-down position during treatment and yet still breath easily. The width of the opening 90 is such that the portions of the face on either side of the nose and mouth rest on the padding 88 of the upper section 80. Thus, the head is supported by the first panel 14 so that the person may be completely relaxed during treatment, which, as discussed below, is important to effective treatment.

Figures 8, 9:
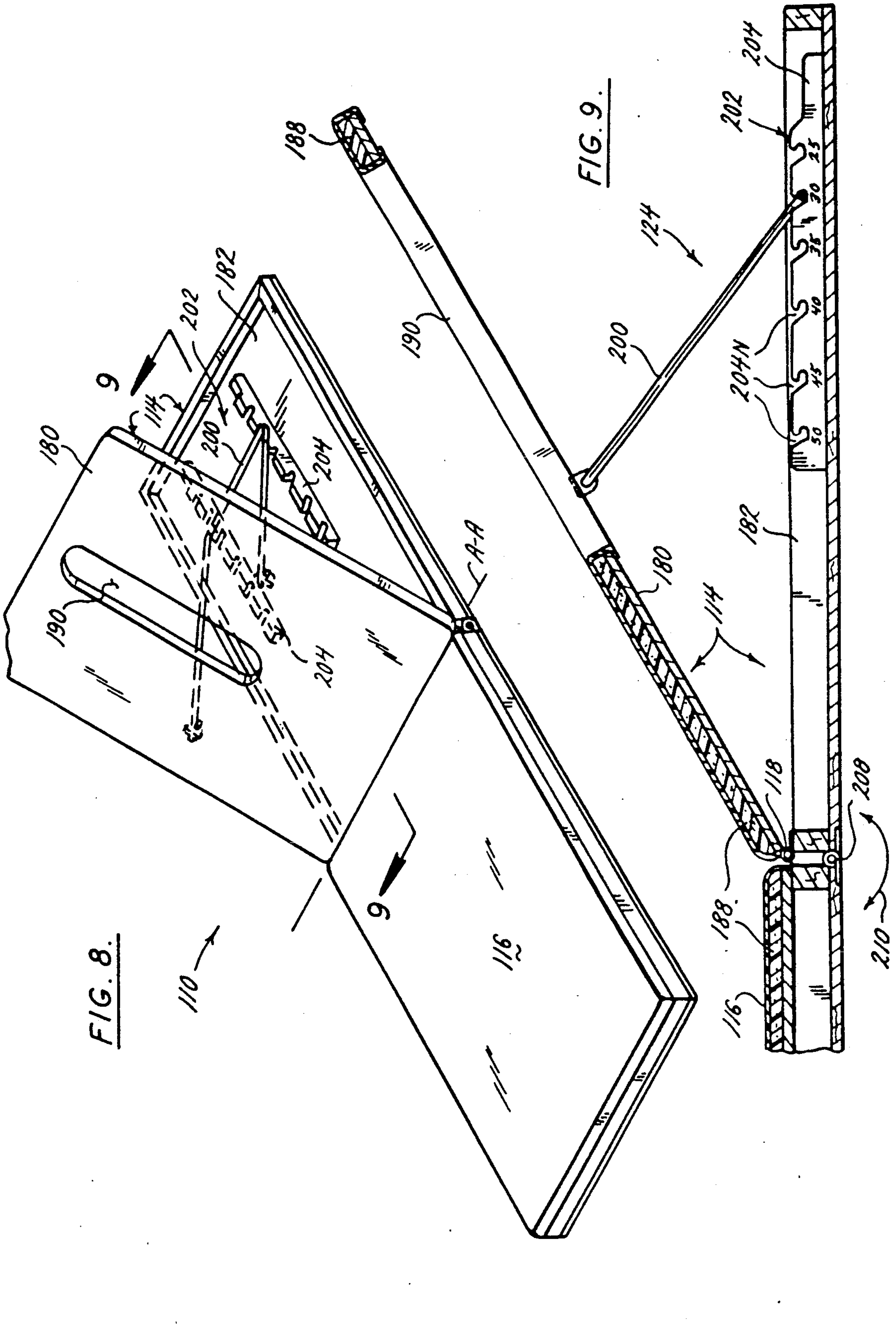
FIG. 8 is a perspective of a device of a second embodiment of the present invention.
FIG. 9 is a section of the device of FIG. 8 taken in the plane including line 9—9 of FIG. 8.

A second, portable embodiment of the device 110 is shown in FIGS. 8 and 9. The portable device includes first and second panels indicated at 114 and 116, respectively, which are abutting in end to end alignment. The upper surfaces of the panels 114, 116 are covered by a layer of padding material 188. As before, the first panel 114 supports the upper portion of the person's body and the second panel 116, the lower portion. The first panel 114 includes a upper section 180, and an lower section 182. The upper section 180 is connected by a hinge 118 to the lower section 182 for pivoting with respect to the lower section and the second panel 116 about a transverse axis AA parallel to and closely adjacent the line of abutment between the first and second panels. The first panel 114 includes an elongated opening 190 for the person's nose and mouth as described in the first embodiment.

Means 124 for holding the first panel 14 and the portion of the person's body supported thereon at a selected angle with respect to the second panel 16 includes a brace member 200 and rack means 202. The brace member is pivotally mounted at its upper end to the underside of the upper section 180. The rack means 202 comprises a pair of laterally spaced bars 204 oriented parallel to the lengthwise extension of the panels 114, 116 and mounted on the lower section 182 of the first panel. The bars 204 have longitudinally spaced notches 204N in them, with each notch 204N in one bar being generally laterally aligned with a corresponding notch in the other bar. Together, a laterally aligned pair of notches 204N constitutes a slot of the rack means 202. In use, the upper section 180 of the first panel 114 is manually pivoted on the hinge 118 upwardly from the lower section 182. The lower end of the brace member 200 is placed in a selected pair of aligned notches 204N. The relative angular position of the first and second panels 114, 116, and thus the approximate angle of extension of the back is marked on the bars 204 adjacent the corresponding notch 204N. The marks constitute means for indicating the approximate degree of extension of the spine in this embodiment. Thus, it may be seen that each pair of notches 204N corresponds to a predetermined angular extension of the spine. The maximum degree of extension available with the portable device is 50°. However, it is to be understood that a greater or less maximum angle of extension may be provided and still fall within the scope of the present invention.

The device 110 of the second embodiment may be collapsed for easily storing and transporting the device. To this end, the lower section 182 of the first panel is connected to the second panel 116 by a hinge 208 located on the bottom of the panels 114, 116 at the line of abutment between the panels. The hinge 208 allows the panels 114, 116 to be folded in the directions indicated by arrow 210 in FIG. 9. Prior to folding the panels 114, 116, the brace member 200 is removed from the notches 204N and folded against the underside of the upper section 180 of the first panel. The upper section 180 is then pivoted down against the lower section 182 and secured by a suitable latch (not shown). The panels 114, 116 are then folded about the hinge 208 and suitable means (not shown) is provided for fastening the panels together in the folded position. A handle (not shown) may be mounted on one end of one of the panels 114, 116 to facilitate holding the device 110.

OPERATION

The function of the first embodiment of the present device 10 may be illustrated by the following example. As previously stated, lower back pain and disability are commonly caused by damage to the intervertebral disc. The damage consists of laceration of circumferential fibers which surround a central mass of gel ("nuclear mass") in the disc. The nuclear mass serves as a fulcrum for bending between the vertebrae. The laceration or tearing of the fibers, which usually occurs in the posterior hemisphere of the disc, results in a shifting of the nuclear mass toward the posterior and posterior-lateral and a tilt of the upper vertebrae toward the anterior and anterior lateral. A victim of this type of injury cannot stand fully erect and may be unable to lie in prone attitude because the protruding nuclear mass at the posterior of the spine prevents the necessary orientation of vertebrae to achieve these positions. To relieve this condition, the nuclear mass must be restored to its normal position between adjacent vertebrae. Sometimes, surgery may be required simply to remove the protruding mass.

The corrective process is enhanced by extending the lower back so as to restore the normal arch of the lumbar spine. Extension of the back closes the space between adjacent vertebrae at the posterior and compresses the displaced mass, encouraging it to move back between the vertebrae. The greater the replacement of nuclear mass between adjacent vertebrae, the greater the angle of extension which may be comfortably assumed by the spine. Normal flexibility in extension generally falls in the range of 55°–60°. Therefore, the device of the first embodiment is adapted to extend the spine to a maximum angle of 60°. It has been found for purposes of treatment that the attainment of 55° of spinal extension is optimal. In order to best facilitate the repositioning of the nuclear mass, the extension of the back should be accomplished passively, that is without the use of the person's back muscles, which permits the intervertebral structures to accommodate the spinal extension.

Treatment of a person having a back injury of the type described above using the device 10 of the present invention is illustrated as follows. The person lies face down on the first and second panels 14, 16 with a portion of his face including his nose and mouth received in the elongate opening 90 in the first panel. The sides of the person's face engage the padded upper section 80 of the first panel 14 on either side of the opening 90 to support his head. The opening 90 is elongated so that persons of different heights may lie on the panels 14, 16 with their noses and mouths received in the opening, and to allow for variations in the longitudinal positioning of persons of the same height. The person is positioned on the panels 14, 16 such that the injured area of the spine is positioned approximately over the transverse axis A, which in both embodiments described herein, closely corresponds to the line of abutment between the panels. The strap 64 is secured over the person's buttocks and tightened down to restrain the person's pelvic region against the second panel 16. The person is then encouraged to relax.

If the person experiences no back pain lying in a horizontal position on the panels 14, 16, one of the cranks 36 is turned to pivot the first panel upwardly a small increment until the person experiences pain. The treatment involves increasing the extension of the spine until a point is reached where back discomfort does not dissipate after a few minutes. This angle of extension is noted by the doctor or therapist so that the progress of treatment may be followed. Several sessions of treatment will usually be necessary.

The second embodiment of the device 110 may be used in tandem with the first device for continued therapy at home between sessions with the doctor or therapist. However, it is to be understood that the second embodiment of the device has other uses unassociated with the specific treatment described herein, such as the relief of discomfort associated with certain back muscle strains. Through the treatment with the device 10 of the first embodiment, the doctor or therapist will have determined an angle of extension which the person should be able to comfortably maintain. The device 110 of the second embodiment may normally be folded up for ease in storage and transportation when not in use. The person unfolds the panels 114, 116 by swinging them apart on the hinge 208 connecting the panels. The upper section 180 of the first panel 114 is swung upwardly about the transverse axis AA on the hinge 118. The lower end of the brace member 200 is placed in a pair of notches 204N in the bars 204 corresponding to the angle of extension of the upper section 180 prescribed by the doctor or therapist.

The person then lies face down on the panels 114, 116 with his nose and mouth received in the opening 190 and attempts to relax, allowing the spine to accommodate the bending in extension. This position is held for a period of time. Although not illustrated, the device 110 may have a strap similar to the strap 64 of the device 10 of the first embodiment for holding the lower portion of the person's body adjacent the line of abutment between the first and second panels against the second panel. In this way, the progress in spinal extension achieved during the treatment sessions with the device of the first embodiment may be maintained between sessions. Even after recovery, the person may periodically use the device 110 of the second embodiment to maintain his full spinal extension. After treatment, the upper section 180 may be pivoted down against the lower section 182, and the panels 114, 116 folded about the hinge 208 in either of the directions indicated by arrow 210 in FIG. 9 to collapse the portable device 110 for storage or transportation It is to be understood that the use of either embodiment of this invention is not limited to treatment of the specific type of back injury described herein.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A device for passive extension of the spine, the device comprising:

first and second support panels abutting in end to end alignment for supporting a person's body in a prone position thereon, the first panel being adapted to pivot with respect to said second panel about a transverse axis generally corresponding to the line of abutment between the panels, the upper portion of the person's body being supported on the first panel, the lower portion of the person's body being supported on the second panel and a selected area of the lumbar or sacrum region of the spine being disposed over the transverse axis;

the first panel being adapted to support the head of the person lying face down thereon while providing clearance for the person's nose and mouth;

means for holding the first panel and the portion of the person's body supported thereon at a selected angular position with respect to the second panel thereby holding the person's spine at a selected angle of extension;

means indicating the approximate degree of extension of the spine; and means generally adjacent the line of abutment between the panels for restraining a portion of the person's body against the second panel.

2. A device as set forth in claim 1 wherein said restraining means comprises a strap adapted to extend over the body and to be secured at opposite sides of the second panel.

3. A device for passive extension of the spine, the device comprising:

first and second support panels abutting in end to end alignment for supporting a person's body in a prone position thereon, the first panel being adapted to pivot with respect to said second panel about a transverse axis, the upper portion of the person's body being supported on the first panel, the lower portion of the person's body being supported on the second panel and a selected area of the lumbar or sacrum region of the spine being disposed over the transverse axis;

the first panel being adapted to support the head of the person lying face down thereon while providing clearance for the person's nose and mouth;

means for holding the first panel and the portion of the person's body supported thereon at a selected angular position with respect to the second panel thereby holding the person's spine at a selected angle of extension; and means indicating the approximate degree of extension of the spine;

the first panel comprising an upper section and a lower section, the upper section being adapted for free translational movement lengthwise of the lower section to accommodate movement of the person's body in the plane of the first panel upon pivoting of the first panel about the said transverse axis.

4. A device for passive extension of the spine, the device comprising: lower first and second support panels abutting in end to end alignment for supporting a person's body in a prone position thereon, the first panel being adapted to pivot with respect to said lower panel about a transverse axis, the upper portion of the person's body being supported on the first panel, the second portion of the person's body being supported on the second panel and a selected area of the lumbar or sacrum region of the spine being disposed over the transverse axis;

the first panel being adapted to support the head of the person lying face down thereon while providing clearance for the person's nose and mouth;

means for holding the first panel and the portion of the person's body supported thereon at a selected angular position with respect to the second panel thereby holding the person's spine at a selected angle of extension; and means indicating the approximate degree of extension of the spine;

the first panel comprising an upper section and a lower section, the upper section being adapted for movement with respect to the lower section to accommodate movement of the person's body in the plane of the first panel, the upper section having pin means depending therefrom adapted to be received in slots in the lower section for guiding movement of the upper section relative to the lower section to generally longitudinally of the lower section.

5. A device for passive extension of the spine, the device comprising:

first and second support panels abutting in end to end alignment for supporting a person's body in a prone position thereon, the first panel being adapted to pivot with respect to said second panel about a transverse axis, the upper portion of the person's body being supported on the first panel, the lower portion of the person's body being supported on the second panel and a selected area of the lumbar or sacrum region of the spine being disposed over the transverse axis;

the first panel being adapted to support the head of the person lying face down thereon while providing clearance for the person's nose and mouth;

means for holding the first panel and the portion of the person's body supported thereon at a selected angular position with respect to the second panel thereby holding the person's spine at a selected angle of extension;

means indicating the approximate degree of extension of the spine;

the first panel comprising an upper section pivotally connected to a lower section at the transverse axis and wherein said holding means comprises a brace member having an upper end and a lower end, the brace member being pivotally mounted at its upper end on the underside of the upper section of the first panel, and elongate rack means extending lengthwise of the first panel and having a plurality of longitudinally spaced slots therein, the lower end of the brace member being receivable in any one of the slots in said rack means, each slot corresponding to a predetermined angular orientation of the first and second panels.

6. A device as set forth in claim 5 wherein said rack means comprises a pair of laterally spaced bars mounted on the lower section of the first panel, the bars each having a plurality of longitudinally spaced notches, and wherein each said slot comprises a pair of laterally aligned notches.

7. A device as set forth in claim 6 wherein the first and second panels are pivotally connected to one another generally along the line of abutment between them for folding the panels together to facilitate transportation and storage of the device.

8. A device for passive extension of the spine, the device comprising:

a base;

first and second support panels abutting in end to end alignment for supporting a person's body in a prone position thereon, the first panel being adapted to pivot with respect to said second panel about a transverse axis, the upper portion of the person's body being supported on one of the panels, the lower portion of the person's body being supported on the other panel and a selected area of the lumbar or sacrum region of the spine being disposed over the transverse axis;

means for pivoting the first panel upwardly about the transverse axis to raise and pivot the portion of the person's body supported thereon, said pivoting means being adapted to hold the first panel and the portion of the person's body supported thereon at a selected angular position with respect to the second panel thereby holding the person's spine in extension.

means for restraining a portion of the person's body generally adjacent the line of abutment between the panels against one of the panels; and means indicating the approximate degree of extension of the spine.

9. A device as set forth in claim 8 wherein the first panel has an elongated opening therein for receiving a portion of the person's face including the nose and mouth, the first panel being thus adapted to support the head of the person while providing clearance for the nose and mouth.

10. A device as set forth in claim 8 wherein said restraining means comprises a strap adapted to extend transversely over the body and to be secured at opposite sides of the base for restraining a portion of the person's body against the second panel.

11. A device as set forth in claim 8 further comprising a stop mounted on the base generally at one end thereof, the stop being engageable with a portion of the person's body to hold the body from sliding toward said one end of the base, and adjustable in a direction parallel to the lengthwise extension of the base.

12. A device as set forth in claim 8 wherein said pivoting means is adapted to hold the first panel at a selected angle in a range from 0° to not substantially greater than 60° with respect to the second panel.

13. A device as set forth in claim 8 wherein the first panel comprises an upper section and a lower section, the upper section being adapted for movement with respect to the lower section to accommodate movement of the person's body in the plane of the first panel.

14. A device as set forth in claim 13 wherein the upper section has pin means depending therefrom adapted to be received in slots in the lower section for guiding movement of the upper section relative to the lower section to generally longitudinally of the lower section.

* * * * *